US010314911B2

(12) United States Patent
Frey, II et al.

(10) Patent No.: US 10,314,911 B2
(45) Date of Patent: Jun. 11, 2019

(54) METHODS FOR PROTECTING AND TREATING TRAUMATIC BRAIN INJURY, CONCUSSION AND BRAIN INFLAMMATION WITH INTRANASAL INSULIN

(71) Applicant: HealthPartners Research & Education, Minneapolis, MN (US)

(72) Inventors: William H. Frey, II, St. Paul, MN (US); Leah Ranae Bresin Hanson, Vadnais Heights, MN (US); Kimberly Byrnes, Gaithersburg, MD (US); Fiona Brabazon, Silver Springs, MD (US)

(73) Assignees: HealthPartners Research & Education, Minneapolis, MN (US); The Henry M. Jackson Foundation for Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 14/679,667

(22) Filed: Apr. 6, 2015

(65) Prior Publication Data
US 2015/0283065 A1  Oct. 8, 2015

Related U.S. Application Data

(60) Provisional application No. 61/976,634, filed on Apr. 8, 2014.

(51) Int. Cl.
| | | |
|---|---|---|
| A61K 38/28 | (2006.01) | |
| A61P 5/50 | (2006.01) | |
| C07K 14/62 | (2006.01) | |
| A61K 45/06 | (2006.01) | |
| A61K 9/00 | (2006.01) | |

(52) U.S. Cl.
CPC .............. *A61K 45/06* (2013.01); *A61K 38/28* (2013.01); *A61K 9/0043* (2013.01)

(58) Field of Classification Search
CPC ................................ C07K 14/62; A61K 38/28
See application file for complete search history.

(56) References Cited

U.S. PATENT DOCUMENTS

| | | | |
|---|---|---|---|
| 2,989,437 A | 6/1961 | Wruble et al. | |
| 5,135,923 A | 8/1992 | Siren | |
| 5,624,898 A | 4/1997 | Frey, II | |
| 5,849,290 A | 12/1998 | Brown et al. | |
| 5,874,573 A | 2/1999 | Winchell et al. | |
| 5,939,395 A | 8/1999 | Yu et al. | |
| 6,113,906 A | 9/2000 | Greenwald et al. | |
| 6,180,603 B1 | 1/2001 | Frey, II | |
| 6,313,093 B1* | 11/2001 | Frey, II | A61K 9/0043 424/400 |
| 6,342,478 B1 | 1/2002 | Frey, II | |
| 6,407,061 B1 | 6/2002 | Frey, II | |
| 6,413,499 B1 | 7/2002 | Clay | |
| 6,544,542 B1 | 4/2003 | Sonoke et al. | |
| 6,576,660 B1 | 6/2003 | Liao et al. | |
| 7,205,276 B2* | 4/2007 | Boderke | A61K 9/0019 514/5.9 |
| 2001/0043915 A1 | 11/2001 | Frey, II | |
| 2001/0047032 A1 | 11/2001 | Castillo et al. | |
| 2002/0028786 A1 | 3/2002 | Frey, II et al. | |
| 2002/0072498 A1 | 6/2002 | Frey, II | |
| 2002/0082215 A1 | 6/2002 | Frey, II | |
| 2002/0133877 A1 | 9/2002 | Kuiper et al. | |
| 2002/0141971 A1 | 10/2002 | Frey, II | |
| 2003/0072793 A1 | 4/2003 | Frey, II et al. | |
| 2003/0165434 A1 | 9/2003 | Reinhard et al. | |
| 2003/0229025 A1 | 12/2003 | Xiao et al. | |
| 2004/0101521 A1 | 5/2004 | Andersen | |
| 2008/0020975 A1 | 1/2008 | Wynick | |
| 2008/0305077 A1* | 12/2008 | Frey, II | A61K 9/0043 424/85.2 |
| 2012/0322727 A1* | 12/2012 | Abdel Maksoud | A61K 31/47 514/6.5 |

(Continued)

FOREIGN PATENT DOCUMENTS

| | | |
|---|---|---|
| WO | WO90/00057 | 1/1990 |
| WO | WO91/07947 | 6/1991 |

(Continued)

OTHER PUBLICATIONS

Anonymous. "Severe TBI Symptoms" www.traumaticbraininjury.com/symptoms-of-tbi/severe-tbi-symptoms/. Published Jul. 27, 2012.*
Anonymous. "Mild TBI Symptoms" www.traumaticbraininjury.com/symptoms-of-tbi/mild-tbi-symptoms/. Published Aug. 18, 2016.*
Anonymous. "Diagnosis" www.traumaticbraininjury.com/symptoms-of-tbi/diagnosis/. Published Jul. 27, 2012.*
Ley et al. "Diabetic Patients With Traumatic Brain Injury: Insulin Deficiency Is Associated With Increased Mortality" J. of Trauma 70: 1141-1144. (Year: 2011).*
Meierhans et al. "Brain metabolism is significantly impaired at blood glucose below 6 mM and brain glucose below 1 mM in patients with severe traumatic brain injury" Critical Care 14:R13 (Year: 2010).*

(Continued)

*Primary Examiner* — Zachary J Miknis
(74) *Attorney, Agent, or Firm* — Barnes & Thornburg LLP; Jeffrey R. Stone

(57) ABSTRACT

The present system is directed in several embodiments to a method of administration of a therapeutic composition for protection of the brain of a subject at risk of injury leading to traumatic brain injury (TBI) and/or treatment of injury to the brain resulting from TBI. The method includes administering one or more therapeutic compositions comprising an effective amount of insulin directly to the subject patient's CNS, with no to minimal systemic exposure. Preferably, this method comprises administration of an effective amount of insulin to the upper third of a patient's nasal cavity, thereby bypassing the patient's blood-brain barrier and delivering the therapeutic composition directly to the patient's central nervous system.

8 Claims, 6 Drawing Sheets

(56) References Cited

U.S. PATENT DOCUMENTS

2013/0090317 A1 4/2013 Vanlandingham et al.
2014/0031280 A1* 1/2014 Frey, II ............... A61K 9/0043
514/6.3

FOREIGN PATENT DOCUMENTS

WO  WO98/42275  10/1998
WO  WO08/62420   5/2008

OTHER PUBLICATIONS

Cerecedo-Lopez et al. "Insulin-associated neuroinflammatory pathways as therapeutic targets for traumatic brain injury" Medical Hypotheses 82:171-174. (Year: 2013).*
Brabazon et al. "Intranasal Insulin Treatment of Traumatic Brain Injury" J. Neurotrauma 31:A-106, Abstract D1-17. (Year: 2014).*
International Preliminary Report on Patentability dated Oct. 20, 2016 for International Application No. PCT/US2015/024621 filed Apr. 7, 2015.
Dezhi et al., "HIF1 alpha upregulation and neuroprotection with deferoxamine in a rat neonatal stroke model" *Pediatric Research*, 55(4): 408A (Apr. 2004).
Ross et al., Intranasal administration of interferon beta bypasses the blood-brain to target the central nervous system and cervical lymph nodes: a non-invasive treatment strategy for multiple sclerosis, *Journal of Neuroimmunology*, 151(1-2): 66-67 (Jun. 2004).
Adachi et al (Brit J Rheumatol 36:255-259, 1997).
Järvinen K and Uritti A. Duration and long-term efficacy of phenylephrine-induced reduction in the systemic absorption of ophthalmic timolol in rabbits. J Ocul. Pharmacol. 1992; 8(2):91-98; abstract only.
Vachharajani NN et al. A pharmacokinetic interactioni study between butorphanol and sumatriptan nasal sprays in healthy subjects: importance of the timing of butorphanol administration. Cephalalgia, 2002; 22:282-287.
Kruck et al., Clin Pharmacol Ther, 48(4): 439-446, Oct. 1990.
Gordon et al., Amer J Med Sci, 297(5): 280-284, May 1989.
Wang and Semenza, Blood, 82(12): 3610-3615, Dec. 15, 1993.
P. Murali Doraiswamy and Anne E. Finefrock, Metals in our minds: therapeutic implications for neurodegenerative disorders, The Lancet Neurology vol. 3, Jul. 2004 (pp. 431-434).
Maxwell and Salniknow, Cancer Biology and Therapy 3(1): 29-35. (Jan. 2004).
Brenneisen et al., The Journal of Biological Chemistry 273(9): 5279-5287. (Feb. 27, 1998).
Crapper McLachlan et al., Lancet 337(8753): 1304-1308. (Jun. 1, 1991).
Chaston and Richardson, American Journal of Hematology 73: 200-210 (2003).
King RG, Med J Aust, 142(6; 352, Mar. 18, 1985).
Youdin et al., Ann NY Acad Sci, 1012:306-325, Mar. 2004.
Lan and Jiang, J Neural Transmission, 104:469-481, 1997.
S. Talegaonkar, P.A. Mishra, Intranasal delivery: An approach to bypass the blood brain barrier, Indian J. Phermacol, Jun. 2004, vol. 36, Issue 3 140-147.
Gould et al., "Glycogen Synthase Kinase-3: A Target for Novel Bipolar Disorder Treatment," Jan. 31, 2004 (Jan. 31, 2004). The Journal of Clinical Psychiatry, vol. 65, Is. 1; p. 1021; especially abstract; p. 13, col. 2, para 3; p. 15, col. 1, para 4 to col. 2, para 1; p. 17, col. 1, para 2.
The Merck Index, Twelfth Edition, 1996, entries 3908 and 7135.
Venters Jr., Homer D. et al., "Heme from Alzheimer's brain inhibits muscarinic receptor binding via thiyl radical generation" Brain Research, 1997, 764, 93-100.
Kornberg, Arthur, et al.; "Inorganic Polyphosphate: A Molecule of Many Functions"; Annual Review Biochemistry, vol. 68: 89-125; Annual Reviews; US 1999.
Frey II, William H. et al.,; "Brain Research 714 (1996) 87-94: Endogenous Alzheimer's brain factor and oxidaized glutathione inhibit antagonist binding to the muscarinic receptor"; Elsevier Science B.V.; US 1996.
Frey II, William H. et al., "Brain Research 655 (1994) 153-160: Inhibitor of antagonist binding to the muscarinic receptor is elevated in Alzheimer's brain"; Elsevier Science B.V.; US 1994.
Otterbein, Leo E., et al.; "Invited Review: Heme Oxygenase: colors of defense against cellular stress"; The American Physiological Society; www.aiplung.orq: US2000.
Rogers et al (Arch Intern Med 158:1021-1031, 1998).
van Beek et al (Biochem Biophys Res Comm 255:491-494, 1999).
Pahan et al (J Clin Invest 100:2671-2679, 1997).
Zhao et al (J Neurosci Res 52:7-16, 1998).
Fawcett et al (Brain Res 950:10-20, 2002).
Atack et al (J Neurochem 60:652-658, 1993).
Liu et al., Molecular and Cellular Biology, Sep. 1992, 3978-3990.
Frey et al., "Delivery of 125I-NGF to the Brain via the Olfactory Route", Drug Delivery, 4:87-92, 1997.
Ostovic et al (Pharm Res 10:470-472, 1993).
Rooijen (Calcif Tissue Int 52:407-410, 1993).
Body et al (Annals of Oncology, 5:359-363, 1994; Abstract Only).
Backstrom et al (J Neurosci 16:7910-7919, 1996).
Brabazon, F., et al., "Intranasal insulin treatment of traumatic brain injury", (Jun. 1, 2014), XP055421658, URL:https://tbitherapy.com/wp-content/uploads/2016/06/neurotrauma-poster-2014-2.pdf.
Brynes, Kimberly R., et al., "FDG-PET imaging in mild traumatic brain injury: a critical review", Frontiers in Neuroenergetics, vol. 5, Jan. 1, 2014 (Jan. 1, 2014), XP055421662, ISSN: 1662-6427, DOI: 10.3389/fnene.2013.00013.
Schilling,Thomas M., et al., "Intranasal insulin increases regional cerebral blood flow in the insular cortex in men independently of cortisol manipulation", Human Brain Mapping, vol. 35. No. 5, Aug. 1, 2013, pp. 1944-1956, XP055421678, ISSN: 1065-9471, DOI: 10.1002/hbm22304.
Extended Search Report dated Nov. 29, 2017 issued by European Patent Office for related application No. 15776436.6.

* cited by examiner

METHODS FOR PROTECTING AND TREATING TRAUMATIC BRAIN INJURY, CONCUSSION AND BRAIN INFLAMMATION WITH INTRANASAL INSULIN

CROSS-REFERENCE TO RELATED APPLICATIONS

This application claims priority to App. Ser. No. 61/976,634, entitled "Method of Treating and/or Preventing Injury to the Brain Caused by Traumatic Brain Injury by Intranasal Administration of Insulin," filed Apr. 8, 2014, the entire contents of which are hereby incorporated by reference in its entirety.

FEDERAL FUNDING

None

BACKGROUND OF THE INVENTION

Field of the Invention

The present invention is directed to methods of protection of the brain of a subject at risk of injury leading to traumatic brain injury (TBI) and/or treating injury to the brain in patients with TBI. More particularly, the present disclosure is directed to a method of protection of the brain of a subject at risk of injury leading to TBI and/or treating TBI by administration of an effective amount of insulin to the upper third of the patient's nasal cavity.

Description of the Related Art

Traumatic Brain Injury (TBI) occurs when sudden trauma causes damage to the patient's brain, e.g., when the head is suddenly and violently hit by an object or when an object pierces the skull and enters the patient's brain tissue.

The most common causes and risk activities for TBI include falls, vehicle crashes and sports injuries. Indirect forces that jolt the brain violently within the skull, e.g., shock waves from a battlefield explosion also may result in TBI as may bullet wounds or other brain-penetrating injuries.

Symptoms of a TBI include unconsciousness, inability to recall the traumatic event, confusion, headache—including a headache that will not go away or worsens with time, lightheadedness, dizziness, blurred vision or tired eyes, ringing in the ears, bad taste in the mouth, fatigue, lethargy, a change in sleep patterns, behavioral or mood changes, trouble with memory, concentration, attention or thinking, repeated vomiting, nausea, convulsions, seizures, an inability to awaken from sleep, dilation of one or both pupils of the eyes, trouble speaking coherently—including slurring of speech, weakness or numbness in the extremities, unsteadiness, lack of coordination, restlessness and agitation.

TBI is a threat to an individual's health in at least the following ways:

(1) TBI has direct effects, a short listing of these are provided above;
(2) Certain TBI's may increase the risk of developing Alzheimer's disease and certain forms of dementia; and
(3) Repeated TBI, such as those that can occur in contact sports such as football, boxing, hockey, lacrosse and soccer to name a few, maybe linked to an increased risk of a dementia known as chronic traumatic encephalopathy.

As defined herein, TBI, in addition to the above, includes concussion injuries; concussions being a type of TBI.

Thus, patients at risk, as referred to herein, may comprise individuals engaged in contact sports who are at risk for head injuries as well as those individuals in professions, e.g., soldiers, police officers, fire fighters, athletes in contact sports and the like, that places them at risk of head injuries leading to TBI.

So far as we are aware, the only preventive, or protective, treatment currently available includes protective gear such as helmets for patients at risk of brain injuries that may lead to TBI. Once TBI is diagnosed, the primary focus and treatment comprises ensuring the patient's brain is properly oxygenated, with sufficient blood flow and control of blood pressure. More severe cases may require treatment involving physical therapy, occupational therapy, speech and language therapy, physical medicine, and psychological and/or psychiatric therapy.

Delivery of the agent and/or composition to the upper one third of the patient's nasal cavity is a means of bypassing the BBB to administer therapeutic compounds and/or agents directly to the CNS. Evidence exists that intranasal treatment with certain therapeutic agent(s) improves, i.e., prevents, protects against and/or treats, a variety of neurological and psychiatric disorders, e.g., stroke, in animals. This basic methodology is discussed and described in U.S. Pat. No. 5,624,898 to Frey II entitled Method for Administering Neurologic Agents to the Brain, as well as in U.S. Pat. No. 6,313,093 to Frey II, the entire contents of each of which are hereby incorporated by reference. This administration technique is a vast improvement over systemic administration methods such as intravenous and oral administration of drugs which generally cannot cross the BBB to reach their targets within the CNS. In addition, Frey's intranasal method is a significant improvement over the general inhalation methods which target the lower two-thirds of the patient's nasal cavity. Both the systemic and general intranasal method targeting the lower two-thirds of the nasal cavity result in a very large, unwanted and potentially dangerous systemic exposure to the administered drug or therapeutic agent(s). The present invention addresses, inter alia, this general intranasal problem as well as ensures that the patient's non-CNS, systemic disease and/or condition is protected from exposure to the therapeutic agent administered to the upper third of the nasal cavity, and potential harm therefrom.

General inhalation methods to the lower two-thirds of the nasal cavity delivered by, e.g., nasal spray bottles, on the other hand, result in a large amount of systemic absorption and exposure, with a very small amount of the administered compound, i.e., less than 5%, making the tortuous journey around the turbinates to the upper third of the nasal cavity and still less compound than that very small amount further bypassing the BBB to actually reach the CNS.

Delivery and administration to the upper third of the nasal cavity, is very effective in administering the subject compounds or agents to the desired target, i.e., the CNS, without significant systemic exposure, though some systemic exposure does occur as is further discussed below.

Unwanted systemic exposure of therapeutics used to treat CNS diseases create several serious problems. The systemic metabolism greatly reduces the bioavailability of any agent and/or compound exposed to the non-CNS system. This reduction of bioavailability is increased by unwanted plasma protein binding of the agent and/or compound. As a result, only a small amount of the active therapeutic agent and/or compound actually reaches the CNS. Because of these, inter alia, issues, the actual dose that must be administered in order to achieve a therapeutic dose in the targeted CNS is far larger than the therapeutic dosing. As a consequence, a relatively large concentration of the agent(s) and/or compounds(s) is in the system and will affect non-target systemic organs and systems. This can create unwanted and often dangerous side effects on these non-target organs and systems, particularly in the specific case of patient's having a systemic, non-CNS disorder or condition that contraindicates the systemic use or exposure of the therapeutic agent(s) needed to treat a CNS-related disorder or condition.

We have addressed the efficiency needs in patent application Ser. No. 12/134,385 to Frey II, et al., entitled "Pharmaceutical Compositions and Methods for Enhancing Targeting of Therapeutic Compounds to the Central Nervous System, the entire contents of which are hereby incorporated by reference, and wherein a vasoconstrictor is administered to the patient's nasal cavity either just prior to, or in combination with, administration of at least one therapeutic agent and/or pharmaceutical composition(s) comprising a therapeutic compound(s) and/or agent(s). The efficiency of the direct administration of the pharmaceutical compound to the CNS, with concomitant reduction of systemic exposure of the pharmaceutical compound is remarkable.

Moreover, we provide disclosure of the following patents and applications, each of which are commonly assigned with the present application and incorporated herein in their entirety for disclosure of, inter alia, the various diseases, conditions or disorders of the CNS relating herein to the first disease or condition of the present invention, as well as various compounds and/or therapeutic agents for treating same by application to the upper ⅓ of the nasal cavity, bypassing of the blood-brain barrier and subsequent direct delivery of the compounds and/or agents to the CNS:

U.S. Pat. No. 7,972,595 Methods and compositions for protecting and treating at least one muscarinic receptor from dysfunction not resulting from oxidative stress, toxic actions of metals or infectious agents by administering a pyrophosphate analog;

U.S. Pat. No. 7,786,166 Methods and compositions for protecting and treating muscarinic receptors through administration of at least one protective agent;

U.S. Pat. No. 7,776,312 Method of treating Alzheimer's disease comprising administering deferoxamine (DFO) to the upper one-third of the nasal cavity;

U.S. Pat. No. 7,618,615 Methods for providing neuroprotection for the animal central nervous system against neurodegeneration caused by ischemia;

U.S. Pat. No. 7,084,126 Methods and compositions for enhancing cellular function through protection of tissue components;

U.S. Pat. No. 6,313,093 Method for Administering Insulin to the Brain;

US Pat Application 20100061959 Methods for Providing Neuroprotecton for the Animal Central Nervous System Against the Effects of Ischemia, Neurodegeneration, Trauma, and Metal Poisoning;

US Patent Application 20080305077 Pharmaceutical Compositions and Method for Enhancing Targeting of Therapeutic Compounds to the Central Nervous System;

US Patent Application 20110311654 Methods and Pharmaceutical Compositions for Treating the Animal Central Nervous System for Psychiatric Disorders;

US Patent Application 20110236365 Method for Protecting and Treating at Least One Muscarinic Receptor From Dysfunction Resulting From Free Radical Damage.

The use of therapeutic agents or compounds that are being used to treat central nervous system (CNS)-related conditions or diseases or disorders such as traumatic brain injury (TBI) may cause unnecessary, unwanted and potentially adverse side effects when given systemically or by general inhalation methods to the lower two-thirds of the patient's nasal cavity. In part, this may occur because systemic uptake dictates that a much larger dose be given, e.g., orally or intravenously, in order to ensure that an effective dose actually crosses the blood-brain barrier and enters the CNS. For example, gastric problems including GI upset, negative effects on blood pressure, and/or cardiac, liver, or kidney toxicity may result from systemic administration. Accordingly, a need exists for a therapeutic agent or compound that may be used to protect the brain of patients potentially at risk of events that place the patients at risk of developing TBI. Further, a need exists for a therapeutic agent or compound that may be used to treat TBI. Further, a need exists for such a therapeutic agent or compound that minimizes the adverse side effects generally associated with administration of drugs used to treat CNS-related disorders. Still further, a need exists for a delivery system for such a composition that provides for enhanced uptake of the composition to maximize the therapeutic affect obtained per administration.

The present invention provides solutions for, inter alia, these problems.

SUMMARY OF THE INVENTION

The present system is directed in one embodiment to a method of administration of a therapeutic composition for protecting the brain of a subject at risk of suffering an injury leading to traumatic brain injury and/or treatment of injury to the brain resulting from traumatic brain injury. The method includes administering one or more therapeutic compositions comprising an effective amount of insulin directly to the subject patient's CNS, with no to minimal systemic exposure. Preferably, this method comprises administration to the upper third of a patient's nasal cavity, thereby bypassing the patient's blood-brain barrier and delivering the therapeutic composition directly to the patient's central nervous system.

DETAILED DESCRIPTION OF THE INVENTION

Definitions

Figure 1:
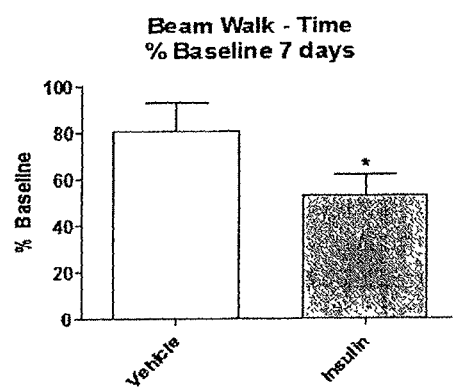
FIG. 1 is a bar graph indicating time for vehicle subjects compared with insulin subjects to traverse beam walk.

As used herein, "central nervous system" (CNS) refers to the brain and spinal cord and associated cells and tissues.

As used herein, "systemic administration" refers to administration of a medication, pharmaceutical and the like by the following non-limited means: oral, intravenous, intra-arterial, intramuscular, epidermal, transdermal, subcutaneous, topic, sublingual as well as general inhalation, i.e., administration to the lower two-thirds of the patient's nasal cavity. In each of these cases, the administered drug will migrate through the patient's circulatory system and, in order to reach the patient's CNS would be required to cross the patient's blood-brain barrier.

In the context of the present invention, the terms "treat" and "therapy" and the like refer to alleviate, slow the progression, prophylaxis, attenuation or cure of existing disease or condition that has or is causing cell death in the CNS.

"Protect", as used herein, refers to putting off, delaying, slowing, inhibiting, or otherwise stopping, reducing or ameliorating the onset of traumatic brain injury (TBI). It is preferred that a large enough quantity of the therapeutic agent(s) and/or compound(s) be applied in non-toxic levels in order to provide an effective level of activity against TBI in subjects, e.g., soldiers, police officers, fire fighters, football players and the like, who are at risk of injury leading to TBI by engaging in violent activities that may lead to head trauma and TBI or related concussive injuries. Consequently, patients or subjects preparing to engage in such violent activities are at risk of injury leading to TBI and may, therefore, receive protective effects from the present invention if administered before actually engaging in said violent activities. Administering an effective amount of insulin to the patient's brain does, as provided below, reduce inflammation within the brain. Administering the invention to the at-risk patient or subject thus provides a higher-than-normal concentration of insulin within the brain during the course of the violent activity, once actually engaged in by the patient or subject. In turn, this concentration of insulin provides protection against inflammation incurred as a result of head trauma, working to reduce the inflammation as soon as it appears. This is in contrast with the patient diagnosed with TBI or other concussive or inflammatory brain condition. The present invention may be used to treat the patient's diagnosed TBI, concussive or inflammatory brain condition.

The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

An "effective amount" of therapeutic agent(s), i.e., insulin, and/or component(s) of the pharmaceutical composition of the present invention comprising therapeutic agent(s) is an amount sufficient to protect against injury to the brain of a subject at risk of injury leading to TBI, treat, reduce and/or ameliorate the symptoms, neuronal damage and/or underlying causes of TBI. In some instances, an "effective amount" may be sufficient to eliminate the symptoms of TBI and overcome the disease itself. Preferably, at least an effective amount of the at least one therapeutic agent, i.e., insulin, and/or component(s) of the pharmaceutical composition yields a tissue concentration in the range of about $10^{-13}$ molar to about $10^{-9}$ molar, but the concentrations may be greater provided that toxicity is avoided. Generally, at least an effective amount of insulin or pharmaceutical composition(s) thereof is administered in order to ensure that an effective amount of insulin is delivered to the target CNS for protection of the brain of a subject at risk of injury leading to TBI and treating TBI.

The concentration range of insulin delivered to the upper third of the patient's nasal cavity may be preferably in the range of $10^{-16}$ molar to about $10^{-6}$ molar in order to yield the preferable tissue concentration range of about $10^{-13}$ molar to about $10^{-9}$ molar, though as discussed above, concentrations in the tissue may be higher so long as toxicity is avoided.

For illustrative purposes only, exemplary treatment regimens relating generally to the therapeutic agent, i.e., insulin, and/or pharmaceutical compounds disclosed herein, including dosage ranges, volumes and frequency are provided below:

Efficacious dosage range for the at least one therapeutic agent, i.e., insulin and/or vasoconstrictors comprises $1 \times 10^{-7}$ to 0.1 mg/kg.

A more preferred dosage range may be $1 \times 10^{-4}$ to 0.1 mg/kg. The most preferred dosage range may be 0.01 to 0.1 mg/kg. The dosage volume (applicable to nasal sprays or drops) range may be 0.015 ml-1.0 mi.

The preferred dosage volume (applicable to nasal sprays or drops) range may be 0.03 ml-0.6 ml.

The brain concentrations that are likely to be achieved with the dosage ranges provided above are for each of the therapeutic agents described above, including insulin, for a single dose: $1 \times 10^{-13}$ to $1 \times 10^{-9}$ M.

The present disclosure is generally directed to administering insulin intranasally to patients for treatment and/or protection of the brain of a subject at risk of injury leading to TBI of traumatic brain injury (TBI).

Generally, the method of the present invention comprises protecting the at-risk brain, or treating TBI with the direct non-invasive delivery of a therapeutic, i.e., effective, amount or dose of insulin, or a pharmaceutical composition thereof, to the CNS. This may be accomplished by administration of at least an effective or therapeutic amount of insulin, or pharmaceutical composition thereof, to the upper one-third of the patient's nasal cavity, thereby delivering the effective or therapeutic amount or dose directly to the patient's CNS, with minimal systemic exposure.

In some embodiments, the therapeutic agent—insulin—may be combined with a vasoconstrictor to be administered intranasally to limit systemic exposure. The vasoconstrictor may be administered to the nasal cavity prior to administration of the therapeutic compound to the upper third, or alternatively to the lower two-thirds, of the nasal cavity or, still more alternatively, the vasoconstrictor and therapeutic compound may be administered concurrently, either to the upper one-third or the lower two-thirds of the patient's nasal cavity. Thus, the present invention allows for a safe and efficacious treatment, or protection of the at-risk brain, of a patient's TBI where systemic administration or exposure is contraindicated.

While not used in conjunction with the treatment of TBI, administration of intranasal insulin has been shown to improve memory in both normal adults and in patients with Alzheimer's disease. Recent studies have shown that insulin may enhance neuronal activity within the medio-temporal lobe and increase performance in humans under in-vivo conditions. Impaired insulin sensitivity may be associated with deficits in verbal fluency and temporal lobe gray matter volume in the elderly.

There are a variety of types of insulin available that may be used in accordance with the present disclosure, including insulins for which zinc is included for stabilization and others which do not include zinc. Because zinc may be detrimental to the olfactory system, insulins that do not contain zinc may be preferable in some cases. Formulations of insulin that either contain no preservatives (which could be prepared for unit dosing) or a safe preservative such as pyrophosphate are preferred. In some embodiments the insulin formulation may not include any phenol or cresol preservatives.

It is preferred that the neurologic agent—insulin—promote nerve cell growth and survival or augment the activity of functioning cells. The neurologic agent may be administered intranasally as a powder, spray, gel, ointment, infusion, injection, or drops, for example. The insulin may be administered in an effective dose. The intranasal composition may be dispensed as a powder or liquid nasal spray, nose drops, a gel or ointment, through a tube or catheter, by syringe, by packtail, by pledget, or by submucosal infusion. Any suitable nasal spray device may be used with embodiments of the present disclosure.

In some embodiments, the composition may include the neurologic therapeutic agent (insulin) as well as a vasoconstrictor that may generally enhance the intranasal therapeutic compound targeting the CNS, as is further described in U.S. patent application Ser. No. 12/134,385, entitled, "Pharmaceutical Compositions and Methods for Enhancing Targeting of Therapeutic Compounds to the Central Nervous System," filed on Jun. 6, 2008, which is hereby incorporated herein in its entirety. As provided in the aforementioned application, constriction of blood vessels resulting from action of the vasoconstrictor in the nasal cavity facilitates transport of the therapeutic compound(s) or agent(s) into the brain along olfactory and trigeminal neural pathways, perivascular pathways, or lymphatic pathways. Thus, intranasal delivery of a therapeutic compound(s) or agent(s) in combination with an agent that constricts blood vessels (i.e. a vasoconstrictor) within or in the proximity of the mucosa of the nasal cavity enhances intranasal drug targeting to, inter alia, the CNS by reducing absorption into the blood, increasing CNS concentrations (as well as other targeted locations), or both.

In one embodiment, the pharmaceutical composition may be comprised of a combination of at least one therapeutic compound comprising insulin and at least one vasoconstrictor. In another embodiment, at least one vasoconstrictor may be applied intranasally or otherwise, i.e., intravenously, topically as a pretreatment or concurrently with administration of at least one therapeutic compound.

Inclusion of vasoconstrictors in intranasal formulations that include insulin for protection of the brain of a subject at risk of injury leading to TBI and/or treatment of TBI may include, but are not limited to providing the following advantages: reducing absorption into the blood, which is desirable for drugs with adverse side effects in the blood or in peripheral tissues; reducing systemic drug exposure, which is important for drugs that are rapidly eliminated in drug metabolizing organs or for drugs that are extensively bound to plasma proteins; targeting drugs to the olfactory epithelium for CNS delivery of drugs; reducing clearance of the drug into the blood from the nasal cavity, which increases the residence time and contact with the nasal epithelium; targeting drugs to the olfactory epithelium, olfactory bulbs and/or anterior olfactory nucleus to have therapeutic potential for the treatment of TBI; targeting high potency drugs to the frontal cortex to reach brain targets involved in cognition disorders, motor dysfunction in TBI; and targeting the hippocampus for treatment of learning and memory disorders associated with TBI.

Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymatazoline, tetrahydrozoline, xylometazoline, clonidine, guanabenz, guanfacine, α-methyldopa, and/or arginine vasopressin.

An at least an effective amount, as herein defined, of the therapeutic compound, i.e., insulin, and/or vasoconstrictor to be administered pursuant to embodiments of the invention is the most preferred method of expression of dosage. Such effective amount is dependent upon many factors, including but not limited to, the type of disease or condition giving rise to an anticipated cerebral ischemia episode, the patient's general health, size, age, and the nature of the treatment, i.e. short-term or chronic treatment.

Generally, the treatment may be given in a single dose or multiple administrations, i.e., once, twice, three or more times daily over a period of time. In some cases, one or more doses daily may be given over an extended period of time, including, months or years.

The method of the invention administers an at least an effective amount of the insulin, or pharmaceutical compound thereof, to the upper third of the nasal cavity of a mammal. It is preferred that the at least an effective amount of insulin be administered to the olfactory area in the upper third of the nasal cavity and particularly to the olfactory epithelium in order to promote transport of the agent into the peripheral olfactory neurons rather than the capillaries within the respiratory epithelium. In some embodiments it may be preferable to transport insulin to the brain by means of the nervous system instead of the circulatory system so that therapeutic agents that are unable to cross the blood-brain barrier from the bloodstream into the brain may be delivered to damaged neurons in the brain.

Transportation Pathway to Bypass Blood-Brain Barrier
The Olfactory Nerve

Various methods of the present invention include administration of at least an effective amount of insulin and/or pharmaceutical composition(s) thereof to tissue innervated by the olfactory nerve and that is located in the upper third of the nasal cavity. The at least an effective amount of insulin and/or pharmaceutical composition(s) thereof can be delivered to the olfactory area via application to the upper third of the nasal cavity.

Fibers of the olfactory nerve are unmyelinated axons of olfactory receptor cells that are located in the upper one-third of the nasal mucosa. The olfactory receptor cells are bipolar neurons with swellings covered by hair-like cilia that project into the nasal cavity. At the other end, axons from these cells collect into aggregates and enter the cranial cavity at the roof of the nose. Surrounded by a thin tube of pia, the olfactory nerves cross the subarachnoid space containing CSF and enter the inferior aspects of the olfactory bulbs. Once the therapeutic agent(s) and/or pharmaceutical composition(s) of the present invention is applied to the upper third of nasal cavity, the therapeutic agent(s) and/or pharmaceutical composition(s) of the present invention can undergo transport through the nasal mucosa and into the olfactory bulb and other areas of the CNS, such as the anterior olfactory nucleus, frontal cortex, hippocampal formation, amygdaloid nuclei, nucleus basalis of Meynert, hypothalamus, midbrain, cerebellum, cervical spinal cord and the like.

Neuronal Transport

Embodiments of the present method includes administration of an at least an effective amount of insulin and/or pharmaceutical composition(s) thereof of the present invention to the subject by application to the upper third of the mammalian subject's nasal cavity. Application of the at least an effective amount of insulin and/or pharmaceutical composition(s) thereof of the present invention in this manner ensures that an effective amount of insulin and/or pharmaceutical composition(s) are transported to the CNS, brain, and/or spinal cord along a neural pathway, with reduced systemic loss and, therefore, minimized systemic exposure. A neural pathway includes transport within or along a neuron, through or by way of lymphatics running with a neuron, through or by way of a perivascular space of a blood vessel running with a neuron or neural pathway, through or by way of an adventitia of a blood vessel running with a neuron or neural pathway, or through an hemangiolymphatic system.

The present invention comprises transportation of the administered insulin and/or pharmaceutical composition(s) thereof by way of a neural pathway, rather than through the circulatory system, so that agent(s) and/or compound(s) that are unable to, or only poorly, cross the blood-brain barrier from the bloodstream into the brain can be delivered to the lymphatic system, CNS, brain, and/or spinal cord. The therapeutic agent(s) and/or pharmaceutical composition(s) of the present invention, once past the blood-brain barrier and in the CNS, can then be delivered to various areas of the brain or spinal cord through lymphatic channels, through a perivascular space, or transport through or along neurons.

Use of a neural pathway to transport a therapeutic agent(s) and/or pharmaceutical composition(s) to the brain, spinal cord, or other components of the central nervous system obviates the obstacle presented by the blood-brain barrier so that medications, i.e., therapeutic agent(s) and/or pharmaceutical compositions of the present invention, that cannot normally cross that barrier, can be delivered directly to the CNS, e.g., the brain and spinal cord. In addition, the present invention can provide for delivery of a more concentrated level of the therapeutic agent(s) and/or pharmaceutical composition(s) of the present invention to the CNS since the therapeutic agent(s) and/or pharmaceutical composition(s) of the present invention do not become diluted in fluids present in the bloodstream. As such, the invention provides an improved method for delivering an effective amount or therapeutic dose of the administered insulin and/or pharmaceutical composition(s) thereof directly to the target CNS including the brain and/or spinal cord.

The Olfactory Neural Pathway

One embodiment of the present method includes delivery of the effective amount of insulin to the subject's CNS for protection of the brain of a subject at risk of injury leading to TBI and treatment of TBI in a manner such that the at least an effective amount of insulin administered to the upper third of the nasal cavity is transported into the CNS, e.g., the brain, and/or spinal cord along an olfactory neural pathway. Typically, such an embodiment includes administering the at least an effective amount of insulin and/or other compound(s) to tissue innervated by the olfactory nerve and inside the nasal cavity. The olfactory neural pathway innervates primarily the olfactory epithelium in the upper third of the nasal cavity, as described above. Application of the at least an effective amount of insulin to a tissue innervated by the olfactory nerve can deliver an effective amount of insulin and/or compound(s) to damaged neurons or cells of the CNS, including but not limited to the brain, and/or spinal cord. Olfactory neurons innervate this tissue and can provide a direct connection to the CNS, brain, and/or spinal cord due, it is believed, to their role in olfaction.

Delivery through the olfactory neural pathway can employ lymphatics that travel with the olfactory nerve to the various brain areas and from there into dural lymphatics associated with portions of the CNS, such as the spinal cord. Transport along the olfactory nerve can also deliver an effective amount of insulin and/or compound(s) to an olfactory bulb. A perivascular pathway and/or a hemangiolymphatic pathway, such as lymphatic channels running within the adventitia of cerebral blood vessels, can provide an additional mechanism for transport of an effective amount of insulin, e.g., to the brain and spinal cord from tissue innervated by the olfactory nerve.

At least an effective amount of insulin, and/or pharmaceutical compositions thereof may be administered to the olfactory nerve, for example, through the olfactory epithelium located at the upper one-third of the nasal cavity. Such administration can employ extracellular or intracellular (e.g., transneuronal) anterograde and retrograde transport of the agent(s) and/or compound(s) entering through the olfactory nerves to the brain and its meninges, to the brain stem, or to the spinal cord. Once the at least an effective amount, i.e., therapeutic dose, of the insulin and/or pharmaceutical composition thereof is dispensed into or onto tissue innervated by the olfactory nerve, the administered insulin and/or pharmaceutical composition and/or components thereof may be transported through the tissue and travel along olfactory neurons into areas of the CNS including but not limited to the brain stem, cerebellum, spinal cord, cerebrospinal fluid, olfactory bulb, and cortical and subcortical structures. Thus, an effective amount of insulin and/or pharmaceutical composition thereof, is delivered to the target CNS for protection of the brain of a subject at risk of injury leading to TBI and/or treatment of TBI.

The blood-brain barrier is bypassed in the present invention by application of at least an effective amount of insulin and/or pharmaceutical composition(s) comprising insulin and/or composition(s) or compound(s) to the upper third of the nasal cavity of the patient, e.g., a mammal. The administered amount of the insulin and/or pharmaceutical composition thereof of the invention migrate from the nasal mucosa through foramina in the cribriform plate along the olfactory neural pathway and an effective amount is delivered directly into the CNS. Further, vasoconstrictors may be applied to the nasal cavity of the patient, either before or during the application of the at least an effective amount of insulin and/or pharmaceutical composition(s) thereof to the upper third of the patient's nasal cavity, to enhance the efficiency of delivery of the an effective amount of insulin to the patient's CNS and minimization of any potential systemic exposure of the administered insulin.

Administration to the nasal cavity employing a neural pathway can thus deliver an effective amount of therapeutic agent(s), e.g., insulin and/or pharmaceutical compositions thereof to the lymphatic system, brain stem, cerebellum, spinal cord, and cortical and subcortical structures of the mammalian patient. The therapeutic agent(s), e.g., insulin and/or pharmaceutical composition(s) thereof of the present invention alone may facilitate this movement into the CNS, i.e., brain, and/or spinal cord. Alternatively, a carrier may assist in the transport of the administered insulin and/or pharmaceutical composition of the present invention into and along the neural pathway. Administration of the insulin and/or pharmaceutical composition(s) thereof of the present invention to the upper third of the mammalian patient's nasal cavity thus enables bypassing of the blood-brain barrier through a transport system from the nasal mucosa and/or epithelium to the CNS, i.e., brain and spinal cord where an effective amount of the administered insulin is delivered.

Various embodiments of the invention administer an at least an effective amount of insulin and/or pharmaceutical composition(s) thereof of the present invention to tissue innervated by the olfactory nerves. Such nerve systems can provide a direct connection between the outside environment and the brain, thus providing advantageous delivery of the agent(s) and/or compound(s) to the CNS, including brain, brain stem, and/or spinal cord. The administered insulin and/or pharmaceutical composition(s) thereof of the present invention may be unable to cross or inefficiently cross the blood-brain barrier from the bloodstream into the brain. Alternatively, for those agent(s) and/or composition(s) that may cross the blood-brain barrier, the present invention offers an alternative treatment for those patients having a concurrent system, non-CNS disease or condition that contraindicates systemic administration of the therapeutic agent(s) and/or compositions(s) needed within the CNS to treat a first CNS-related disease, condition or disorder. Thus, the methods of the present invention allow for the delivery of an effective amount of insulin and/or pharmaceutical composition(s) thereof to the target CNS by way of the olfactory nerve rather than through the circulatory system in order to facilitate protection of the brain of a subject at risk of injury leading to TBI and/or treatment of TBI. Thus, this method of administration of at least an effective amount of insulin to the upper third of the nasal cavity and delivery of the effective amount of insulin to the target CNS allows for the efficient and non-invasive delivery of an effective amount of insulin and/or pharmaceutical composition(s) thereof of the present invention to the CNS, brain, or spinal cord without systemic loss or exposure.

Alternative Pathways

Alternative non-systemic pathways to the olfactory nerve pathway discussed above comprise pathways along other nerves that innervate the nasal cavity, e.g., the trigeminal pathway, well known to the skilled artisan.

Administration of Therapeutic Agents) and/or Pharmaceutical Compounds

Administering insulin according to the methods of the invention for protection of the brain of a subject at risk of injury leading to TBI and/or treatment of TBI may include application of at least an effective amount of the therapeutic agent, i.e., insulin alone or formulating the at least an effective amount of insulin with at least an effective amount of one or more of the compounds described supra as pharmaceutical compositions and administering the pharmaceutical compositions to a mammalian subject or host, including a human patient, intranasally to the upper third of the nasal cavity. The therapeutic agent(s) and/other components of the pharmaceutical composition thereof, e.g., vasoconstrictor may be administered at one of a variety of doses sufficient to provide an effective amount at the desired point of action in the CNS for the administered at least an effective amount of insulin and/or pharmaceutical composition component.

As noted, vasoconstrictor(s) may be delivered as pre-treatment, co-treatment and/or post-treatment with the therapeutic agent(s) and/or pharmaceutical composition, either alone or as a component of the pharmaceutical composition. Delivery of at least an effective amount of insulin in this manner results in delivery of an effective amount of insulin to the target CNS with maximum efficiency in the delivery of insulin, i.e., with minimal to no systemic exposure of insulin.

For application to the upper third of the nasal cavity as suspensions, aerosols, sprays or drops, the at least an effective amount of insulin and/or pharmaceutical composition(s) can be prepared according to techniques well known in the art of pharmaceutical formulation. The compositions can be prepared as suspensions of the agent(s) in solutions which may comprise salts such as saline, components such as phosphate, succinate or citrate buffers to maintain pH, osmoregulatory and osmotic agents such as taurine, and suitable preservatives, absorption promoters to enhance bioavailability, fluorocarbons or other solubilizing or dispersing agents known in the art. The means of applying a pharmaceutical composition intranasally to the upper third of the nasal cavity may be in a variety of forms such as a powder, spray, gel or nose drops.

Other forms of compositions for administration of the at least an effective amount of insulin and/or pharmaceutical compositions or elements thereof include a suspension of a particulate, such as an emulsion, a liposome, or in a sustained-release form to prolong the presence of the pharmaceutically active agent in an individual. The powder or granular forms of the pharmaceutical composition may be combined with a solution and with a diluting, dispersing or surface-active agent. Additional compositions for administration include a bioadhesive to retain the agent at the site of administration at the upper third of the nasal cavity, for example a spray, paint, or swab applied to the mucosa. A bioadhesive can refer to hydrophilic polymers, natural or synthetic, which, by the hydrophilic designation, can be either water soluble or swellable and which are compatible with the pharmaceutical composition. Such adhesives function for adhering the formulations to the mucosal tissues of the upper third of the nasal cavity. Such adhesives can include, but are not limited to, hydroxypropyl cellulose, hydroxypropyl methylcellulose, hydroxy ethylcellulose, ethylcellulose, carboxymethyl cellulose, dextran, gaur gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and combinations thereof. The composition can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampoules.

The pharmaceutical composition may be formulated in a sustained-release form to prolong the presence of the active therapeutic agent(s) in the treated individual. Many methods of preparation of a sustained-release formulation are known in the art and are disclosed in Remington's Pharmaceutical Sciences. Generally, the therapeutic agent(s), pharmaceutical composition and/or components of the pharmaceutical composition, i.e., vasoconstrictor may be entrapped in semipermeable matrices of solid hydrophobic polymers. The matrices can be shaped into films or microcapsules. Matrices can include, but are not limited to, polyesters, copolymers of L-glutamic acid and gamma ethyl-L-glutamate, polylactides, polylactate polyglycolate, hydrogels, non-degradable ethylene-vinyl acetate, degradable lactic acid-glycolic acid copolymers, and alginic acid suspensions. Suitable microcapsules can also include hydroxymethylcellulose or gelatin and poly-methyl methacrylate. Microemulsions or colloidal drug delivery systems such as liposomes and albumin microspheres can also be used.

Delivery Systems

The therapeutic agent, i.e., insulin, and/or a pharmaceutical composition comprising at least an effective dose of insulin and/or components of the pharmaceutical composition of the present invention may further be dispensed and applied to the upper third of the nasal cavity as a powdered or liquid nasal spray, suspension, nose drops, a gel, film or ointment, through a tube or catheter, by syringe, by packtail, by pledget (a small flat absorbent pad), by nasal tampon or by submucosal infusion. In some aspects of the present invention, the methods comprise administering to an individual the at least an effective dose of insulin and/or a pharmaceutical composition thereof to the upper third of the nasal cavity by way of a delivery device. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. In some aspects, an accurate effective dosage amount is contained within a bioadhesive patch that is placed directly within and on the upper third of a nasal cavity.

At least an effective dose of insulin and/or a pharmaceutical composition comprising at least an effective dose of insulin and/or components of the therapeutic composition of the present invention may be conveniently delivered to the upper third of the nasal cavity in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the therapeutic agent(s) and/or pharmaceutical composition as will be readily recognized by the skilled artisan. In the case of a pressurized aerosol, the dosage unit may be controlled by providing a valve to deliver an accurately metered amount.

The means to deliver the at least an effective amount of insulin or pharmaceutical composition comprising the at least an effective amount of insulin and/or components of the pharmaceutical composition of the present invention to the upper third of the nasal cavity as a powder may be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the upper third of the nasal cavity.

Intermittent and Cyclic Dosing

In various embodiments of the invention, therapeutic agent, i.e., insulin, and/or a pharmaceutical composition comprising at least an effective amount of insulin and/or the components of the pharmaceutical composition may be administered as a single and one-time dose, or alternatively the at least an effective amount of insulin and/or the components of the pharmaceutical composition may be administered more than once and intermittently. By "intermittent administration" is intended administration of at least an effective amount of insulin and/or the components of the pharmaceutical composition, followed by a time period of discontinuance, which is then followed by another administration of the at least effective amount, and so forth. Administration of the at least an effective amount of insulin and/or the components of the pharmaceutical composition may be achieved in a continuous manner, as for example with a sustained-release formulation, or it may be achieved according to a desired daily dosage regimen, as for example with one, two, three, or more administrations per day. By "time period of discontinuance" is intended a discontinuing of the continuous sustained-released or daily administration of the insulin and/or the components of the pharmaceutical composition. The time period of discontinuance may be longer or shorter than the period of continuous sustained-release or daily administration. During the time period of discontinuance, the concentration(s) of insulin and/or the components of the pharmaceutical composition level in the relevant tissue is substantially below the maximum level obtained during the treatment. The preferred length of the discontinuance period depends on the concentration of the effective dose and the form of therapeutic agent(s) and/or the components of the pharmaceutical composition used. The discontinuance period can be at least 2 days, preferably is at least 4 days, more preferably is at least 1 week and generally does not exceed a period of 4 weeks. When a sustained-release formulation is used, the discontinuance period must be extended to account for the greater residence time of the at least one therapeutic agent at the site of injury. Alternatively, the frequency of administration of the effective dose of the sustained-release formulation can be decreased accordingly. An intermittent schedule of administration of insulin and/or the components of the pharmaceutical composition may continue until the desired therapeutic effect, and ultimately treatment of the disease or disorder is achieved.

In yet another embodiment, intermittent administration of the at least an effective amount(s) of insulin and/or the components of the pharmaceutical composition is cyclic. By "cyclic" is intended intermittent administration accompanied by breaks in the administration, with cycles ranging from about 1 month to about 2, 3, 4, 5, or 6 months. For example, the administration schedule might be intermittent administration of the at least an effective dose of insulin and/or the components of the pharmaceutical composition, wherein a single short-term dose is given once per week for 4 weeks, followed by a break in intermittent administration for a period of 3 months, followed by intermittent administration by administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of administration of insulin and/or the components of the pharmaceutical composition to a subject may continue until the desired therapeutic effect, and ultimately treatment of the disorder or disease is achieved.

Working Example

In a reduction to practice of one embodiment of the present invention, a Moderate Controlled Cortical Impact Injury Model, developed for use in establishing a Traumatic Brain Injury (TBI) model was employed. In this study, adult male Sprague Dawley rats were subjected to a controlled cortical impact as that procedure is described in "A mouse model of sensorimotor controlled cortical impact: characterization using longitudinal magnetic resonance imaging, behavioral assessments and histology". Onyszchuk G, Al-Hafez B, He Y Y, Bilgen M, Berman N E, Brooks W M. J Neurosci Methods. 2007 Mar. 15; 160(2):187-96. Onyszchuk, G., et al., J. Neurosci. Methods, 2007, 160(2): p. 187-196, the contents of which are hereby incorporated by reference.

Procedure

Following the controlled injury using the TBI model described above, the injured rats received either saline or insulin under anesthesia by isoflurane. A first dose of either saline (saline rats) or insulin (insulin rats) was delivered 4 hours post-injury to the upper third of the nasal cavity as described above in connection with the present invention. Thereafter, doses of saline or insulin were administered once a day for 7 to 14 days to the upper third of the nasal cavity. Motor function was evaluated in the saline rats and with the insulin rats. In addition, immunohistochemistry and Western Blot analyses were performed with a focus on inflammatory cells, microglia, and neuronal survival.

Results

Blood was taken from the tail vein of a small cohort of rats (n=3 per treatment group) immediately prior to injury, 4 hours after injury/immediately before treatment and 3 hours after treatment. The results indicate no significant difference in blood glucose between the two groups, shown in FIG. 5. Consequently, the administration of insulin to the upper third of the nasal passage does not significantly affect the patient's blood glucose.

In addition, both the saline rats and the insulin rats were weighed on days 1, 7, 14 and 21 post-injury. The results indicate no significant difference in weight between the two groups. Consequently, the administration of insulin to the upper third of the nasal passage does not significantly affect the patient's weight.

Motor function tests consisting of a beam walk and a peg walk, both tests well-established measures of functional deficit and recovery in preclinical TBI research, also given to the saline rats and the insulin rats on days 1 and 7 post-injury. The results for the beam walk, shown in FIG. 1, indicate a significant decrease in time for the insulin rats to cross the beam as compared with day 1 baseline results and as compared with the saline (vehicle) rats performance on day 7.

Figure 2:
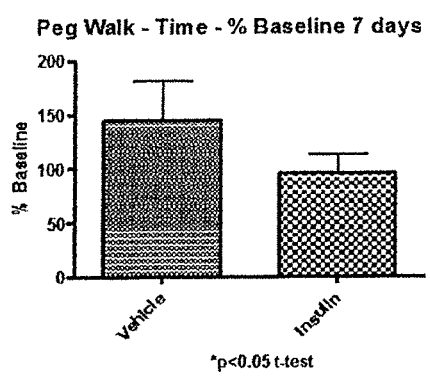
FIG. 2 is a bar graph indicating time for vehicle subjects compared with insulin subjects to traverse the peg walk.

The peg walk results illustrated in FIG. 2 indicate a positive trend towards improved motor function in the insulin rat group from baseline results from day 1 as well as when compared with saline (vehicle) rats on day 7. Thus, intranasal insulin, administered according to the present invention to the upper third of the nasal cavity in subjects with TBI results in improved motor function in those subjects.

Figure 5:
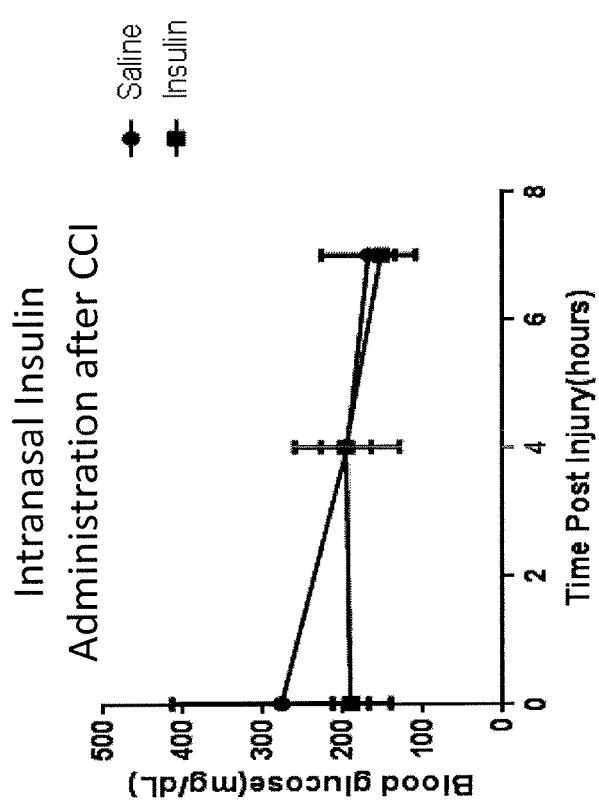
FIG. 5 is a line graph indicating a lack of change in blood glucose after intranasal insulin delivery (injury–CCI–completed at time=1 h, insulin or saline administered at time=4 h; final blood draw at time=7 h)

Blood glucose levels were also tested following intranasal insulin delivery. FIG. 5 illustrates a lack of change in blood glucose after intranasal insulin delivery (injury–CCI–completed at time=1 h, insulin or saline administered at time=4 h; final blood draw at time=7 h).

Figure 6:
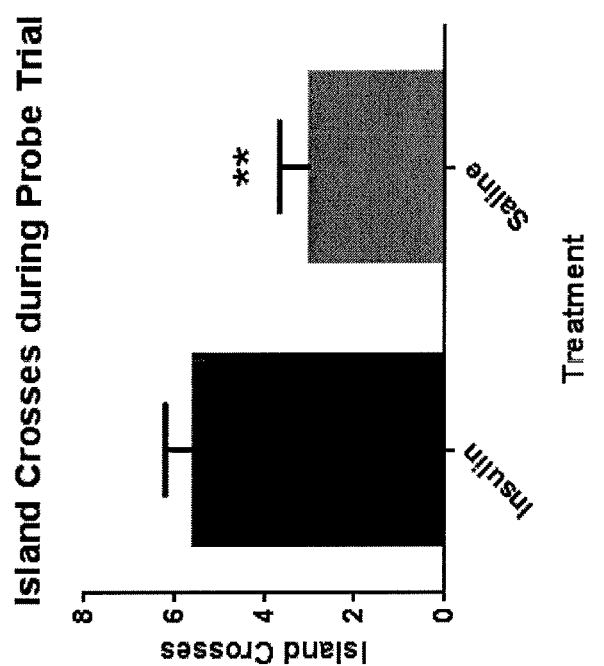
FIG. 6 is a bar graph indicating number of target island crosses for vehicle subjects compared with insulin subjects in Morris water maze probe trial.
Figure 7:
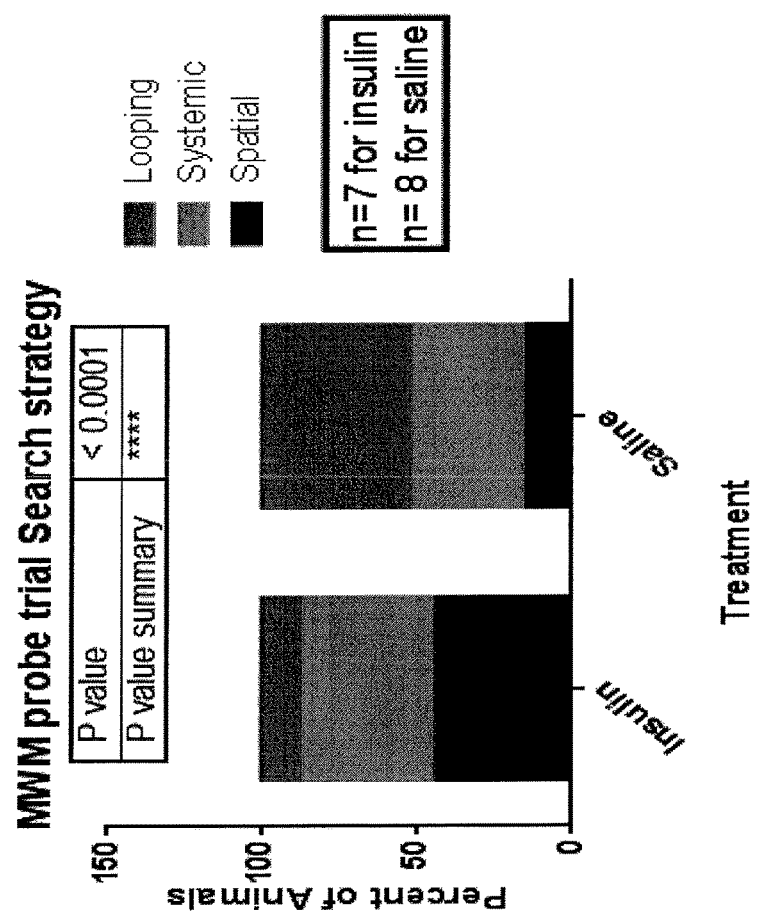
FIG. 7 is a bar graph indicating search strategy analysis for vehicle subjects compared with insulin subjects in Morris water maze probe trial.

Cognitive function was also tested in saline (vehicle) and insulin treated rats on days 11-14 post-injury, using the well-known and well-justified Morris water maze task. Memory retention was assessed using the probe trial portion of the task, and showed that insulin-treated rats had a significant increase in the number of crosses of the target island region in comparison to saline (vehicle) treated rats, where they had been previously trained to exit the maze, as shown in FIG. 6. In addition, search strategy, which indicates method of searching the maze for the exit island, shown in FIG. 7, demonstrates that saline (vehicle) treated rats utilized significantly less targeted search methods (looping) than insulin rats.

Figure 8A:
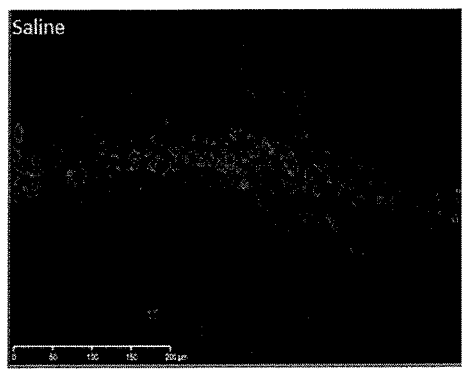
FIG. 8a is a line graph illustrating neuronal viability in the saline rat hippocampus.
Figure 8B:
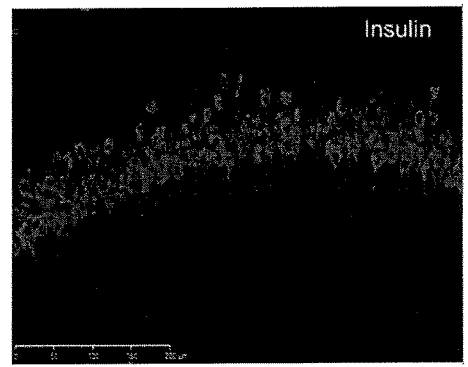
FIG. 8b is a line graph illustrating improved neuronal viability in the insulin rat hippocampus compared with the saline rat hippocampus.

In addition to the above motor and cognitive function tests, the effect of insulin administered to the upper third of the nasal cavity in the insulin rat group as compared with the saline rat group was also evaluated by using an immunohistochemical marker of neurons, specifically NeuN, to examine the effect of the insulin on neurons in the hippocampus post-injury after sacrifice on day 8. FIGS. 8a and 9b are photographs that indicate, following a quantitative assessment according to well-known methods, an improved neuronal viability in the hippocampus of the intranasal rats as compared with the saline rats. FIG. 8a illustrates neuronal viability in the saline rat hippocampus. FIG. 8b illustrates an improved neuronal viability in the insulin rat hippocampus, as illustrated by the brighter and more robust neuronal presence as compared with the saline rat of FIG. 8a.

Finally, the effect of insulin administered as in the Working Example on microglia was evaluated post-injury and following sacrifice on day 8 for the saline rats and the insulin rats. Microglia are the macrophages of the brain, with two dominant phenotypes: M1 and M2.

M1 microglia are classically activated pro-inflammatory cells. M1 microglia are useful in the initial healing process, but persistent activation results in neuronal cell death due to production of reactive oxygen species. M2 microglia are anti-inflammatory, pro-healing macrophages.

Figure 3:
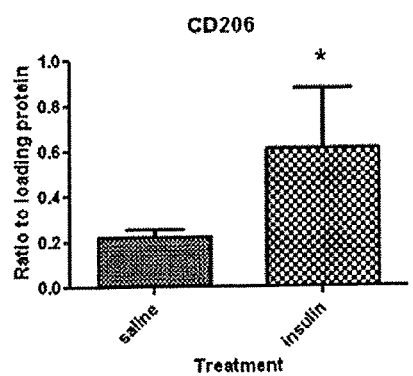
FIG. 3 is a bar graph indicating expression of CD206 in vehicle subjects compared with insulin subjects.
Figure 4:
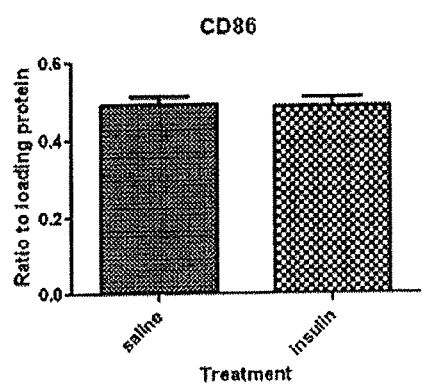
FIG. 4 is a bar graph indicating expression of CD86 in vehicle subjects compared with insulin subjects.

The Working Example results, illustrated in FIGS. 3 and 4 indicate a significant increase in M2 microglia, characterized by expression of CD206, in the intranasal rats as compared with the intranasal saline rats as shown in FIG. 3. There was no significant increase in expression of M1 microglia markers, characterized by expression of CD86 and as illustrated in FIG. 4. This indicates, inter alia, that the insulin regimen according to the present invention and as used in the Working Example is pushing the microglia toward the M2 anti-inflammatory phenotype. Thus, subjects with TBI that are treated with insulin administered to the upper third of the subject's nasal cavity experience an increase in activation of anti-inflammatory cells, specifically M2 microglia cells which, in turn promote healing of the damaged cells in the subject with TBI, or protect against damage to the brain of a subject at risk of injury to the brain leading to TBI.

Further, inflammation is a major, and damaging, component of neurodegenerative central nervous system disorders, including but not limited to Alzheimer's disease, Parkinson's disease, ALS, Huntington's disease, to name a few. As a result, the discovery that intranasal insulin increases the M2 anti-inflammatory microglia phenotype in the brain of a patient experiencing neuroinflammation in the brain as a result of brain injury or other neurodegenerative disorder, condition and/or disease is applicable and useful to protect, prevent and/or treat such inflammation.

CONCLUSION

The Working Example indicates that insulin administered to the upper third of the patient's nasal cavity, increases neuronal viability in the hippocampus, increased the formation of anti-inflammatory M2 microglia which promote healing, and increased motor and cognitive functional recovery after Traumatic Brain Injury (TBI).

In addition, the results of the Working Example indicate that insulin delivered to the brain of patients with brain injury or other neurodegenerative disorder involving inflammation of the brain can be used to reduce the associated inflammation by increasing production of the M2 anti-inflammatory phenotype in the patient's brain. Certainly, neurodegenerative disorders such as Alzheimer's disease, Parkinson's disease, Huntington's disease, ALS involve inflammation of the brain and are, therefore, amenable to treatment using the present invention. In addition, patients at risk of developing a neurodegenerative condition and/or disease leading to neuroinflammation may be identified and the neuroinflammation prevented, or protected against.

The invention has been described with reference to various specific and preferred embodiments and techniques. However, it should be understood that many variations and modifications may be made while remaining within the spirit and scope of the invention.

We claim:

1. A method for treating traumatic brain injury (TBI) in a patient, comprising:
    administering a therapeutic agent consisting of at least an effective amount of insulin to the upper third of the nasal cavity of the patient, and thereby enabling at least an effective amount of insulin to directly access the patient's central nervous system by bypassing the blood-brain barrier; and
    treating the patient's TBI by protecting the patient's brain from inflammation and reducing inflammation in the patient's brain by increasing the expression of anti-inflammatory M2 microglia cells in the patient's brain.

2. The method of claim 1, further comprising administering the insulin to a tissue innervated by the olfactory nerve, wherein the administered insulin bypasses the blood-brain barrier to access the patient's central nervous system to treat the TBI.

3. The method of claim 2, further comprising the administered insulin bypassing the blood-brain barrier by migrating along a neural pathway into the patient's central nervous system to treat the patient's TBI.

4. The method of claim 1, wherein the administered insulin comprises a non-zinc insulin.

5. The method of claim 1, further comprising pretreating the patient's nasal cavity with an effective amount of at least one vasoconstrictor before administering the insulin to the upper third of the patient's nasal cavity.

6. The method of claim 1, wherein the at least an effective amount of insulin is in the range of $1\times10^{-7}$ to 0.1 mg/kg, with reference to the patient's body weight.

7. The method of claim 6, wherein the range for the at least an effective amount of insulin is $1\times10^{-4}$ to 0.1 mg/kg, with reference to the patient's body weight.

8. The method of claim 1, wherein the concentration of insulin in the brain of the patient after a single dose is in the range of $1\times10^{-13}$ to $1\times10^{-9}$ molar.

* * * * *